United States Patent [19]
Yonemori et al.

[11] Patent Number: 5,270,173
[45] Date of Patent: Dec. 14, 1993

[54] METHOD OF MONITORING CELL CULTURE

[75] Inventors: Fumihiko Yonemori; Masayoshi Yamaguchi, both of Osaka, Japan

[73] Assignee: Sumitomo Electric Industries, Ltd., Osaka, Japan

[21] Appl. No.: 900,791

[22] Filed: Jun. 22, 1992

Related U.S. Application Data

[63] Continuation of Ser. No. 368,308, Jun. 6, 1989, abandoned.

[51] Int. Cl.$^5$ .......................... C12Q 1/02; C12Q 1/44; C12Q 1/26; C12M 3/00
[52] U.S. Cl. .......................................... 435/29; 435/19; 435/25; 435/284; 435/291
[58] Field of Search ..................... 435/29, 19, 25, 284, 435/291

[56] References Cited

U.S. PATENT DOCUMENTS

| | | |
|---|---|---|
| 3,805,239 | 4/1974 | Watanabe .......................... 340/146 |
| 3,973,239 | 8/1976 | Kakumoto et al. .................. 340/146 |
| 4,882,346 | 11/1989 | Driscoll et al. . | |

FOREIGN PATENT DOCUMENTS 59-78681  5/1984  Japan .
60-225284 11/1985  Japan .

*Primary Examiner*—Christine M. Nucker
*Assistant Examiner*—D. R. Preston
*Attorney, Agent, or Firm*—Cushman, Darby & Cushman

[57] ABSTRACT

A method of monitoring cell culture which comprises digitizing an image of cultured cells inputted to an image processing equipment through a TV camera connected with an observing means and measuring the number and cell proliferation of cultured cells by a processing with using a spatial filter, can treat a large amount of cells in a short time and give a precise number of the cells.

12 Claims, 3 Drawing Sheets

Fig. 3

| 0 | 0 | -k | -k | -k | 0 | 0 |
|---|---|---|---|---|---|---|
| 0 | -k | $\ell$ | $\ell$ | $\ell$ | -k | 0 |
| -k | $\ell$ | $\ell$ | $\ell$ | $\ell$ | $\ell$ | -k |
| -k | $\ell$ | $\ell$ | $\ell$ | $\ell$ | $\ell$ | -k |
| -k | $\ell$ | $\ell$ | $\ell$ | $\ell$ | $\ell$ | -k |
| 0 | -k | $\ell$ | $\ell$ | $\ell$ | -k | 0 |
| 0 | 0 | -k | -k | -k | 0 | 0 |

$k > 0,\ \ell > 0$

Fig. 4

| j | -i | -h | -g | -h | -i | j |
|---|---|---|---|---|---|---|
| -i | -f | e | d | e | -f | -i |
| -h | e | c | b | c | e | -h |
| -g | d | b | a | b | d | -g |
| -h | e | c | b | c | e | -h |
| -i | -f | e | d | e | -f | -i |
| j | -i | -h | -g | -h | -i | j |

$a \geq 0,\ b \geq 0,\ c \geq 0,\ d \geq 0,\ e \geq 0,$
$f \geq 0,\ g \geq 0,\ h \geq 0,\ i \geq 0,\ j \geq 0$

Fig. 5

| 0 | 0 | -1 | -1 | -1 | 0 | 0 |
|---|---|---|---|---|---|---|
| 0 | -1 | 1 | 1 | 1 | -1 | 0 |
| -1 | 1 | 1 | 1 | 1 | 1 | -1 |
| -1 | 1 | 1 | 1 | 1 | 1 | -1 |
| -1 | 1 | 1 | 1 | 1 | 1 | -1 |
| 0 | -1 | 1 | 1 | 1 | -1 | 0 |
| 0 | 0 | -1 | -1 | -1 | 0 | 0 |

Fig. 6

| 0 | -1 | -2 | -3 | -2 | -1 | 0 |
|---|---|---|---|---|---|---|
| -1 | -3 | 0 | 2 | 0 | -3 | -1 |
| -2 | 0 | 4 | 5 | 4 | 0 | -2 |
| -3 | 2 | 5 | 7 | 5 | 2 | -3 |
| -2 | 0 | 4 | 5 | 4 | 0 | -2 |
| -1 | -3 | 0 | 2 | 0 | -3 | -1 |
| 0 | -1 | -2 | -3 | -2 | -1 | 0 |

METHOD OF MONITORING CELL CULTURE

This is a continuation of application Ser. No. 07/368,308, filed on Jun. 6, 1989, which was abandoned.

FIELD OF THE INVENTION

The present invention relates to a method of monitoring cell culture. More particular, it relates to a method of monitoring cell culture which comprises digitizing a cultured cell image inputted to an image processing equipment and measuring the number of living cells, the number of dead cells and the cell proliferation by a processing using a spatial filter.

BACKGROUND ARTS

When cells are cultivated in a vessel such as a microplate, dish or culturing bottle, some of living cells die if a concentration of the living cells becomes so high as to reach a so-called "full growth" state. To prevent this, it is necessary to change a culture medium and/or to subculture the cells before the full growth state is reached. Hitherto, a technician determines a timing when the cell culture solution is changed or the subculturing is started with his skill by observing the cell proliferation of the cells in the vessel through a microscope. However, such conventional method is not quantitative and therefore not accurate in determining the cell proliferation of cultured cells and the concentration of living cells. In addition, it is time-consuming and has difficulty in precisely observing the cell proliferation of a large amount of cultured cells.

Further, when cells are cloned by a limiting dilution-culture method or when cells are fractionated, both the number of living cells and that of dead cells should be simultaneously measured. In such cases, even if a blood cell counter is used, visual measurement with the microscope includes large error and takes a lot of time.

A cell detection method using image processing has been proposed instead of visual observation with the microscope. However, it has low detection efficiency since it is done simply by binary digitizing. Although detection of the cells is easy when a background is simple, for example, in case of an agar medium on which colonies are formed, a pattern of the cells and the background are both complicated since the cells in the culturing vessel contain dead cells, dust or other foreign substances.

OBJECTS OF THE INVENTION

An object of the present invention is to provide a method of monitoring cell culture by which the number of the cells can be precisely measured when the pattern of the cells and the background are complicated.

Another object of the present invention is to provide a method of monitoring cell culture which can treat a large amount of cells in a short time.

CONSTITUENTS OF THE INVENTION

According to the present invention, there is provided a method of monitoring cell culture which comprises digitizing an image of cultured cells inputted to an image processing equipment through a TV camera connected with an observing means and measuring the number and cell proliferation of cultured cells by a processing with using a spatial filter.

The method of monitoring cell culture according to the present invention will be illustrated by making reference to the accompanying drawings.

By using TV camera connected with a microscope as an observing means, an image of cultured cells in a culturing vessel is inputted to an image processing equipment. According to the procedures shown in FIG. 1, the image is processed and the number of living cells is counted. Preferably, expansion processing is carried out after the binary digitizing. According to a procedure as shown in FIG. 2, the number of living cells and the number of dead cells are measured.

By displacing the focus from an entirely focused state, the image of the cultured cells is inputted at a focus point where a center area of cultured living cells is brighter and a circumferential area thereof is darker so that an image has a clear profile. By displacing the focus of the microscope in a distance of ±5 to ±250 micrometers, the image of the living cell has such clear profile. When the displaced distance is less than 5 micrometers, the whole image of the living cell remains dark. When the displaced distance is more than 250 micrometers, the image is blurred.

In this state, when an image of one cultured living cell is magnified by such magnification that the cell image inscribes a square of a spatial filter matrix having a designated size, that is, when the spatial filter matrix has the size of $n \times n$ pixels ($n \geq 5$), the image of the cultured cell is inputted at such magnification that one pixel has a size of $10/n \times 10/n$ to $21/n \times 21/n$ (micrometer x micrometer) since one cultured living cell generally has a size of 10 to 21 micrometers. The detection efficiency is poor when the living cell is larger or smaller than the spatial filter matrix of a designated size. The spatial filter matrix having the size of not smaller than $5 \times 5$ pixels is used. When the spatial filter matrix having the size of smaller than $5 \times 5$ pixels is used, the filter has poor detection efficiency and cannot be used practically.

When the whole image is filtered through the round shape spatial filter having negative coefficients in its circumferential area, positive coefficients in its center area and zero coefficients in other intermediate areas, the living cell parts can be emphasized. For example, the shape and coefficients of the spatial filter having $7 \times 7$ pixels are shown in FIG. 3.

The coefficients and shape of the filter for emphasizing the living cell parts can be optimized by collecting brightness distribution patterns of the images of plural objective living cells and determining an average pattern of them. The reason for the above is that since the spatial filtering emphasizes the parts which have better correlation with the shape of the spatial filter (standard pattern), the best correlation is realized when the shape of the spatial filter coincides with the cell brightness pattern. For example, the shape and coefficients of the optimized spatial filter having $7 \times 7$ pixels are shown in FIG. 4.

in this case, a value $y_{ij}$ of the center pixels is calculated according to the following equation:

$$y_{ij} = \frac{1}{A} \sum_{m=-3}^{+3} \sum_{n=-3}^{+3} h_{mn} x_{i+m, j+n}$$

wherein
x is a value of the pixel before filtering,
y is a value of the pixel after filtering, A is a coefficient, and $h_{mn}$ is a coefficient corresponding to each pixel of the filter.

The pixels are binary digitized with a suitable threshold. The pixel in which the living cell is present is digitized to be "1" and the pixel in which no living cell is present is digitized to be "0". The optimized binary digitized threshold is determined so that in one image, a visually counted number or actual number of the living cells coincides with the number of masses of the pixels which are digitized as "1" and considered to have the living cell, and an average value of these in plural images can be used as a fixed binary digitized threshold. The reason for this is that the correlation of the shape is observed irrespective of background brightness. From the number of the pixels which are considered to have the living cell (the number of the pixels which are digitized as "1"), the number of the living cells is calculated. Since the number of the pixels which one living cell occupies is constant, the number of the living cells is calculated according to the following equation:

$$\text{The number of the living cells} = \frac{\text{The number of the pixels which are considered to have the living cells}}{\text{The number of the pixels which one living pixel occupies}}$$

It is possible to decrease the error which is caused when the number of the pixels is converted to the number of the cells, by subjecting the binary digitized image to a 4-neighbor expansion processing, 8-neighbor expansion processing or combination thereof one or more times before calculating the number of the pixels from the binary digitized image. By the expansion processing, the images which are damaged by binary digitizing can be restored, and the number of the pixels which one cell occupies is increased so that influence of one pixel is decreased.

The image emphasized by spatial filtering is binary digitized again with a threshold different from, usually lower than, the threshold which is used to determine the number of the living cells and then inverted. The pixel in which the dead cell is present is digitized to be "1" and the pixel in which no dead cell is present is digitized to be "0". From the number of the pixels which are considered to have the dead cell (the number of pixels which are digitized as "1"), the number of the dead cells is calculated. Since the number of the pixels which one dead cell occupies are constant, the number of the dead cells is calculated according to the following equation:

$$\text{The number of the dead cells} = \frac{\text{The number of the pixels which are considered to have the dead cells}}{\text{The number of the pixels which one dead pixel occupies}}$$

The circumferential area (profile) of the living cell may be contained also in the pixel of dead cell depending on the absolute value of the threshold. This is removed by a procedure wherein the spatially filtered image is binary digitized with the threshold for determining the number of dead cells and then inverted, and an binary digitized image which is binary digitized with the threshold for determining the number of living cells or an binary digitized image which is subjected to an expansion processing suitable times is deducted from said inverted image on the display. The expansion processing is carried out preferably several times. When the expansion processing is carried out too many times, the necessary image are erased. In the same manner as for the living cells, the error which is caused when the number of the cells is calculated from the number of pixels is reduced by subjecting the binary digitized image from which the noise of the circumferential area of the living cell is removed to a 4-neighbor expansion processing, 8-neighbor expansion processing or combination thereof one or more times.

EFFECTS OF THE INVENTION

By the combination of input of the image at the focus point where the center area of the living cells is brighter and the circumferential area thereof is darker and intensification of the living cell image with the spacial filter, it is possible to extract the cells having the shape and characteristics of the living cells, so that the separation of the living cells and the dead cells is easily done. Thereby, the accurate measurement of the cell number by extracting the cultured living cells present in the complicated pattern and background. In addition, a large amount of the cells can be treated in a short time.

Therefore, timing of the change of the culture medium or the start of subculture can be determined quickly and precisely.

Now, the present invention is explained by following examples.

EXAMPLE 1

A complicated image in which colonies of cultured living cells are present together with dead cells, foreign substances and the like was inputted to an image processing equipment PIAS-1 (available from PC Systems, Japan) through a microscope connected with a CCD camera by displacing a focus in a distance of 30 micrometers from an entirely focused state.

The magnification was such that a profile of cultured living cell inscribed a spatial filter having 7×7 pixels, that is, one pixel had a size of 1.8 micrometers×1.8 micrometers.

When the image was digitized with the image processing equipment PIAS-1 and filtered with a spatial filter having shape and coefficients shown in FIG. 5, a detection rate was 67 % and 70 with an erroneous detection rate of 10 % and 20 %, respectively. The detection rate and the erroneous detection rate were determined according to the following equations:

$$\text{Detection rate} = \frac{\text{The number of the actually present living cells which are detected by the image processing}}{\text{The number of living cells actually present in the original image}}$$

$$\text{Erroneous detection rate} = \frac{\text{The number of the living cells considered to be present by the image processing but not actually present in an original image}}{\text{The number of all living cells which are considered to be present by the image processing}}$$

EXAMPLE 2

A complicated image in which colonies of cultured living cells are present with dead cells, foreign substances and the like was inputted to an image processing equipment PIP-4000 (available from ADS Limited, Japan) through a microscope connected with a CCD camera by displacing a focus in a distance of 30 micrometers from an entirely focused state.

The magnification was such that a profile of cultured living cell inscribed a spatial filter having 7×7 pixels, that is, one pixel had a size of 2.4 micrometers×2.4 micrometers.

The image was digitized with the image processing equipment PIP-4000 and filtered with the spatial filter having shape and coefficients shown in FIG. 6. When the binary digitizing threshold which is based on the visually counted number of living cells is used, the detection rate was 73 % and 81 % with the erroneous detection rate of 10 % and 20 %, respectively. When the same image was subjected to the binary digitizing alone, the detection rate was 57 % and 60 % with the erroneous detection rate of 10 % and 20 %, respectively.

The image in which living cells and dead cells were randomly present was inputted in the same manner as the above, and the number of the living cells and that of the dead cells were measured. As to the living cells, the visually counted number was 47 and the number measured by the image processing was 50, and then an error was 6.4 As to the dead cells, the visually counted number was 453 and the number measured by the image processing was 453, and then the error was 0 %. Further, the error of the measured number of total cells (the number of the living cells and that of the dead cells) had a standard deviation of ±10.2 % in one sigma for 39 samples. The error was determined according to the following equation:

$$\text{Error} = \frac{\text{(The number measured by image processing)} - \text{(The visually counted number)}}{\text{The visually counted number}}$$

EXAMPLE 3

The procedure as in Example 2 was repeated except that the binary digitizing threshold based on the actual number of the living cells was used instead of the binary digitizing threshold based on the visually counted number of the living cells. When the image was filtered with the spatial filter having the same shape and coefficients as used in Example 2, the detection rate was 73 % and 82 % in the erroneous detection rate of 10 % and 20 %, respectively.

When the binary digitized image was subjected to 8neighbor expansion processing once, the error caused by converting the number of the pixels to the number of the living cell was 8 %. It was 17 % when the image had not been subjected to the expansion processing.

BRIEF DESCRIPTION OF THE DRAWINGS

FIG. 3 shows shape and coefficients of a spatial filter having 7×7 pixels;

FIG. 4 shows shape and coefficients of an optimized spatial filter having 7×7 pixels; and FIGS. 5 shows shape and coefficients of spatial filters used in Example 1.

FIG. 6 shows shape and coefficients of spatial filters used in Example 2.

Figure 1:
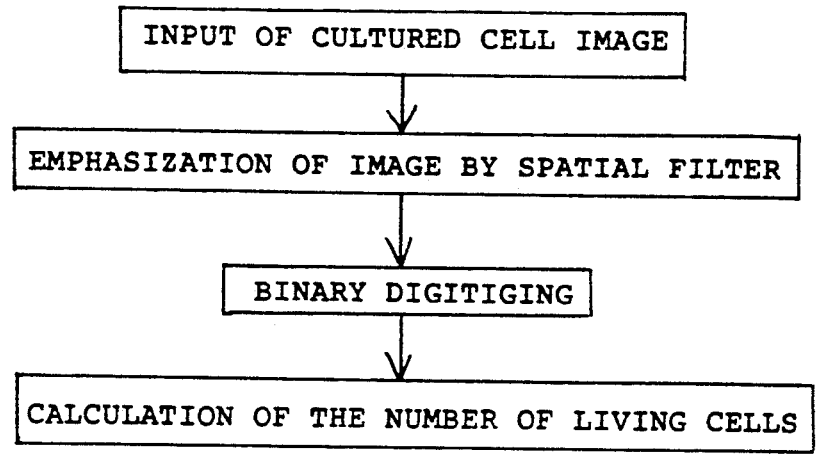
FIG. 1 is a flow chart of procedures for measuring the number of living cells.
Figure 2:
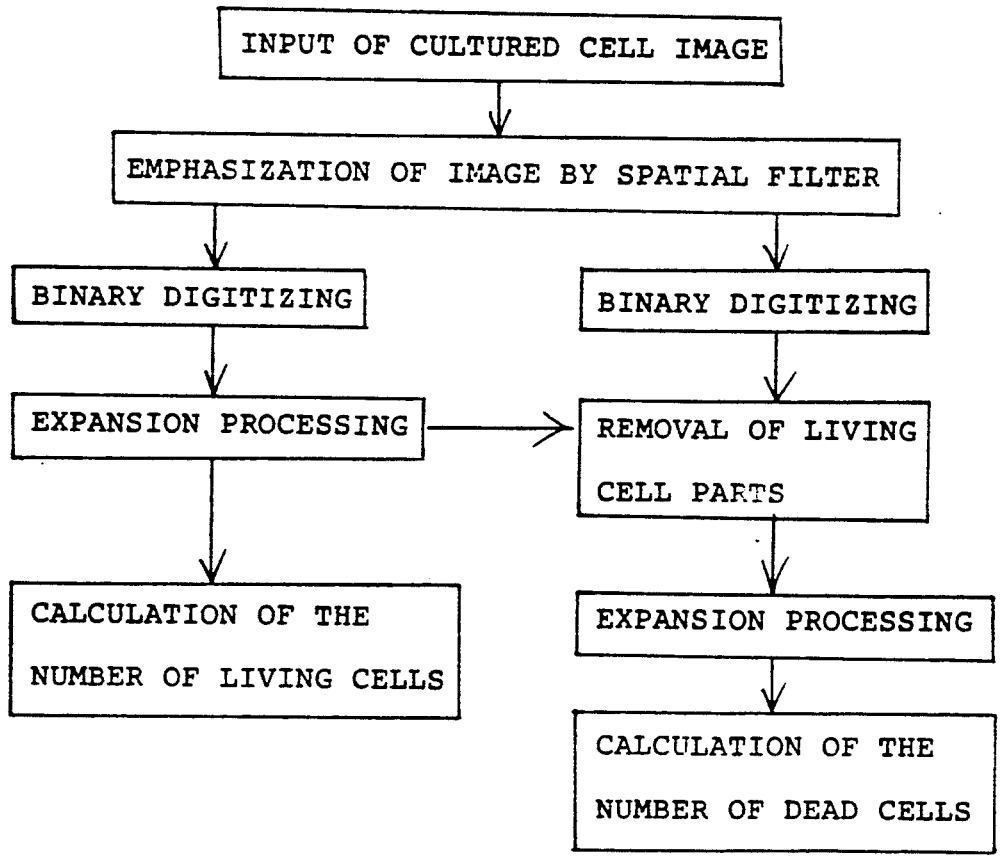
FIG. 2 is a flow chart of procedures for measuring the number of living cells and that of dead cells.

What is claimed is:

1. A method of monitoring cell culture comprising the steps of:
    forming optical images of cultured cells using a microscope while displacing the focus of the microscope to enhance the profile of living cells;
    electronically imaging said optical images using a TV camera to form electronic images;
    measuring cell brightness distribution patterns and averaging them;
    spatially filtering said electronic image of cultured cells wherein the coefficients and shape of said spatial filter applied are determined algorithmically using the average pattern of cell brightness distribution patterns;
    binary digitizing said spatially filtered image by setting threshold limits for live and dead cell components;
    distinguishing living cells by processing said digitized images; and
    measuring the number of living cells,
    wherein said cell culture comprises attachment-dependent eukaryotic cells.

2. A method of monitoring cell culture comprising the steps of:
    forming optical images of cultured cells using a microscope while displacing the focus of the microscope to enhance the profile of living cells;
    electronically imaging said optical images using a TV camera to form electronic images;
    measuring cell brightness distribution patterns and averaging them;
    spatially filtering said electronic image of cultured cells wherein the coefficients and shape of said spatial filter applied are determined algorithmically using the average pattern of cell brightness distribution patterns;
    binary digitizing said spatially filtered image by setting threshold limits for live and dead cell components;
    distinguishing living cells by processing said digitized images; and
    measuring the number of living cells and the number of dead cells,
    wherein said cell culture comprises attachment-dependent eukaryotic cells.

3. The method of monitoring cell culture according to claim 2, wherein a focus is displaced from an entirely focused state and the image of the cultured cells is inputted at a focus point where center area of cultured living cells is brighter and circumferential area thereof is darker so that an image has a clear profile.

4. The method of monitoring cell culture according to claim 3, wherein the image of cultured cells is inputted at the focus point where the focus is displaced in a distance of ±5 to ±250 micrometers from the entirely focused state.

5. The method of monitoring cell culture according to claim 1 or 2, wherein the spatial filter has a size of n×n pixels (n≧5).

6. The method according to claim 5, wherein the image of cultured cells is input in such magnification that one pixel has a size of N/n (wherein N (μm) is an average diameter of the cultured cells).

7. The method of monitoring cell culture according to any one of claims 1 or 2, wherein the image processed with the spatial filter is binary digitized and the number of the cultured living cell is calculated according to the following equation:

$$\text{The number of the living cells} = \frac{\text{The number of the pixels which are considered to have the living cells}}{\text{The number of the pixels which one living pixel occupies}}$$

8. The method of monitoring cell culture according to claim 7, wherein binary digitized thresholds in plural images are determined so that the visually measured number or actual number of living cells in one image is the same as the number of masses which are considered to have the living cells and then the binary digitizing is carried out by using an average value of the binary digitized thresholds as a fixed binary digitized threshold.

9. The method of monitoring cell culture according to any one of claim 7, wherein the spatially filtered image is binary digitized and subjected to a 4-neighbor expansion processing, 8-neighbor expansion processing or combination thereof one or more times and then the number of living cells is calculated from that of pixels.

10. The method of monitoring cell culture according to claims 1 or 2, wherein the spatially filtered image is binary digitized with a threshold lower than the threshold which is used to determine the number of living cells and then inverted, and the number of dead cells is calculated according to the following equation:

$$\text{The number of the dead cells} = \frac{\text{The number of the pixels which are considered to have the dead cells}}{\text{The number of the pixels which one dead pixel occupies}}$$

11. The method of monitoring cell culture according to claim 10, wherein the spatially filtered image is binary digitized with the threshold for determining the number of dead cells and then inverted and an binary digitized image which is binary digitized with the threshold for determining the number of living cells or an binary digitized image which is subjected to an expansion processing suitable times is deducted from said inverted image on the display, thereby parts corresponding to the dead cells are extracted.

12. The method of monitoring cell culture according to claim 10, wherein the binary digitized image in which parts corresponding to the dead cells are extracted is subjected to a 4-neighbor expansion processing, 8-neighbor expansion processing or combination thereof one or more times before the number of the dead cells is calculated.

* * * * *